(12) United States Patent
Chepuri et al.

(10) Patent No.: US 9,145,364 B2
(45) Date of Patent: Sep. 29, 2015

(54) SYNTHESIS OF PSUEDO INDOXYL DERIVATIVES

(71) Applicant: Council of Scientific & Industrial Research, New Delhi (IN)

(72) Inventors: Venkata Ramana Chepuri, Pune (IN); Yogesh Mansukhabhai Goriya, Pune (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/245,376

(22) Filed: Apr. 4, 2014

(65) Prior Publication Data
US 2014/0309434 A1    Oct. 16, 2014

(30) Foreign Application Priority Data

Apr. 15, 2013    (IN) .......................... 1113/DEL/2013

(51) Int. Cl.
*C07D 209/36*    (2006.01)
*C07D 209/96*    (2006.01)

(52) U.S. Cl.
CPC ............ *C07D 209/96* (2013.01); *C07D 209/36* (2013.01)

(58) Field of Classification Search
None
See application file for complete search history.

(56) References Cited

FOREIGN PATENT DOCUMENTS

WO    WO/2012/081893    6/2012

OTHER PUBLICATIONS

Goriya, et al., Chem. Comm., 49:6376 (2013).*
Ardakani et al.; "Based-Induced Intramolecular Cyclisation of O-Azidophenyl Sec-Alkyl Ketones"; Tetrahedron Letters No. 49; 1979; pp. 4769-4772.
Zhang et al.; "Regiodivergent Annulation of Alkynyl Indoles to Construct Spiro-pseudoindoxyl and Tetrahydro-β-carbolines"; Organic Letters, vol. 13, No. 13; 2011; pp. 3458-3461.
Lunazzi et al.; "Unexpected Stereodynamic Consequences of the Restricted Rotations in *ortho*-Acyl- and *ortho*-Vinyl Biphenyls"; The Journal of Organic Chemistry; No. 71; 2006; pp. 9297-9301.
Korn et al.; "Colbalt-Catalyzed Cross-Coupling Reactions of Heterocyclic Chlorides with Arylmagnesium Halides and of Polyfunctionalized Arylcopper Reagents with Aryl Bromides, Chlorides, Flourides and Tosylates"; Synthesis; 2006; pp. 3547-3574.
Tietze et al.; "Efficient Synthesis of the Structural Core of Tetracyclines by a Palladium-Catalyzed Domino Tsuji-Trost-Heck-Mizoroki Reaction"; Chem. Eur. J.; No. 14; 2008; pp. 2527-2535.
Chavan et al.; "A Highly Diastereoselective Total Synthesis of (±)-Heritonin and (±)-heritol"; Tetrahedron 68; 2012; pp. 8509-8514.
Pandey et al.; "Total Synthesis of (±)-Sacidumlignan D$^§$"; The Journal of Organic Chemistry; No. 76; 2011; pp. 2315-2318.

* cited by examiner

*Primary Examiner* — Michael Barker
(74) *Attorney, Agent, or Firm* — Blank Rome LLP

(57) ABSTRACT

The patent discloses novel 2,2-disubstituted 1,2-dihydro-3H-indol-3-one derivatives and their preparation thereof.

11 Claims, 3 Drawing Sheets

SYNTHESIS OF PSUEDO INDOXYL DERIVATIVES

REFERENCE TO RELATED APPLICATION

This application claims the priority of Indian Patent Application No. 1113/DEC/2013, filed Apr. 15, 2013, which is incorporated herein by reference.

TECHNICAL FIELD OF THE INVENTION

The present invention relate to one pot Cu-catalysed synthesis of 2,2-disubstituted 1,2-dihydro-3H-indol-3-one (trivially known as pseudo indoxyl) compounds of Formula 2 from α-bromophenyl sec-alkyl/sec-alkenyl ketones comprising $S_NAr$ with azide and Smalley cyclization. Particularly, present invention relates to compound of Formula 2 useful as intermediate in the synthesis of many natural products and biologically active small molecules, find applications in the areas of fluorescence dyeing and in solar cell with Stokes shift greater than 80 and absorption in IR region.

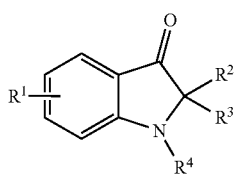

Formula 2

BACKGROUND AND PRIOR ART OF THE INVENTION 2,2-disubstituted 1,2-dihydro-3H-indol-3-one (trivially known as pseudo indoxyl) is one of the important structural units present in many natural products and biologically active small molecules[1]. Apart from their use as intermediates in the synthesis of natural products, in recent years, the indol-3-one derivatives have also found important applications in the areas of fluorescence dyeing and in solar cell applications.

Rearrangement of 2,3-dihydroxyindolines and 3H-indol-3-ols (acid-, base-, or thermal-induced) is one of the earlier methods reported for the preparation of indoxyl derivatives. The oxidative rearrangements of 2,3-disubstituted indoles or the tetrahydrocarbolines is one of more popular methods used in the synthesis of the indoxyl class of natural products. The addition of Grignard reagents to 2-arylindolone followed by the acid catalysed pinacol rearrangement, as well as the addition of carbon cantered nucleophiles to spiro[furan/pyran-2,2'-indolin]-3'-ones are some of the methods which offer the provision to vary the substituents at the C(2) position.

The CuI catalyzed intramolecular amination, an interrupted Ugi reaction comprising of an internal attack of the electron rich aromatic ring on an electrophilic nitrilium ion, the gold-mediated cycloisomerization of 2-alkynyl aryl azides, the Mannich/Henry reaction of cyclic α-carbonyl ketimines and the reaction of amino acids with arynes are some of the other methods that have been developed recently for synthesis of 2,2-disubstituted indolin-3-ones.

In 1979, Ardakani and Smalley in M. A. Ardakani and R. K. Smalley, Tetrahedron Lett., 1979, 20, 4769; reported the base induced intramolecular cyclization of αazidophenyl sec-alkyl ketones leading to 2,2-disubstituted indolin-3-ones trivially known as the Smalley cyclization (eq. 1, Scheme 1). This reaction has served as the key step in the total synthesis of lapidilectineB. The substrates that are generally used for the Smalley Rearrangement require free fabricated α-azidophenyl sec-alkyl ketones.

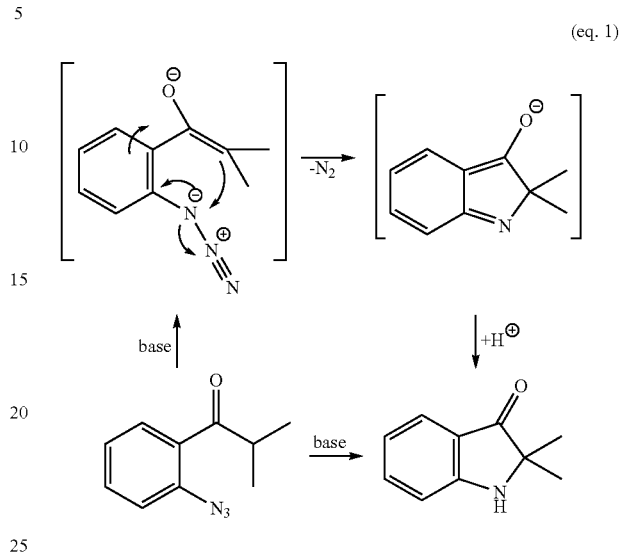

(eq. 1)

WO 2012081893 A2 discloses the marked derivatives 3-indole rinon, the following formula 1 or 2, or his or her salt:

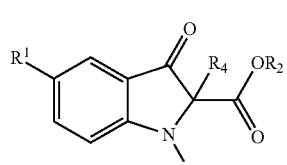

[Formula 1]

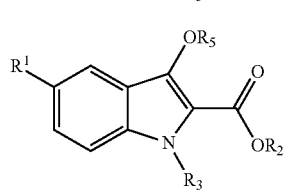

[Formula 2]

$R_1$ is hydrogen, $C_{1-6}$ alkoxy, $C_{1-4}$ alkyl, substituted or unsubstituted $C_{2-6}$ alkenyl, oxy, benzyloxy or $C_{1-4}$ alkoxy, and phenyl; $R_2$ is $C_{1-6}$ alkyl; $R_3$ and $R_4$ are each independently hydrogen, $C_{1-6}$ alkyl, $C_{1-4}$ alkyl, substituted or unsubstituted $C_{2-6}$ alkenyl, $C_{2-6}$ alkynyl, benzyl, or $C_{3-6}$ cycloalkyl methyl; $R_5$ is a substituted or unsubstituted $C_{1-6}$ alkyl, $C_{1-4}$ alkyl, $C_{2-6}$ alkenyl or $C_{3-6}$ cycloalkyl methyl.

Regiodivergent Annulation of Alkynyl Indoles To Construct Spiro-pseudoindoxyl and Tetrahydro-β-carbolines by Yong-Qiang Zhang et. al in Org. Lett., 2011, 13 (13), pp 3458-3461 reports Regiodivergent annulations of 3-phenoxy alkynyl indoles have been developed and tuned by protective groups through gold catalysis. With electron-donating protective groups, the substrate followed a C3-selective annulation and gave structurally interesting tetrahydro-β-carboline derivatives possessing potential bioactivity. Using electron-withdrawing protective groups, the substrate underwent a C2-selective annulation and afforded the structurally useful spiro-pseudoindoxyl found in natural indole alkaloids. Notably, an interesting and unusual 1,2-migration of the phenoxy group was found in the C3-selective process.

However, the reported methods adopted multistep sequences with harsh reaction conditions in some particular cases.

The present inventors have recently documented one pot $S_NAr$-click reaction of fluoronitrobenzenes with azide nucleophile for synthesis of 1,4 substituted triazoles. It is further reported that if there is no dipolarophile to trap the azide, these intermediate azide are reduced further to anilines. With the current interest to provide a more feasible, cost effective process for the synthesis of natural products having the indolin-3-one core, the invention is directed to provide a process using one-pot [Cu]-catalysed $S_NAr$ and the Smalley rearrangement of α-halophenyl sec-alkyl ketones.

OBJECTS OF THE INVENTION

Main object of the present invention is to provide a cost effective, industrially feasible process using one-pot [Cu]-catalysed $S_NAr$ and the Smalley cyclization of α-halo phenyl sec-alkyl ketones to obtain compounds of formula 2.

Another object of the present invention is to provide 2,2-disubstituted 1,2-dihydro-3H-indol-3-one (trivially known as pseudo indoxyl) compounds of Formula 2 with Stokes shift greater than 80 and absorption in IR region which are useful as intermediate in the synthesis of many natural products and biologically active small molecules, find applications in the areas of fluorescence dyeing and in solar cell.

SUMMARY OF THE INVENTION

Accordingly, present invention provides a one pot, one step process for preparation of compound of Formula 2,

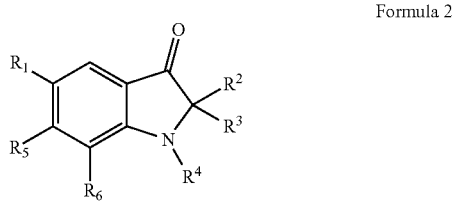

Formula 2 wherein,
$R^1$ represents independently H, —OMe, N—OH, halo, alkyl (C1-C5) and NR(2)
wherein R is selected from the group consisting of H, O, alkyl(C1-C5) and aryl);
$R_2$ represents independently alkyl(C1-C5), aryl, —CN, —CO$_2$Et, vinyl(CH=CH$_2$);
R3 represents independently alkyl(C1-C5), vinyl; or
R2 and R3 cyclize to form —CH2-(CH$_2$)$_n$—CH2— where n is 4, 5, 6;
R4 represents independently hydrogen, alkyl, —(CH$_2$)$_n$—Ar, —(CH$_2$)$_n$—CN, —(CH$_2$)$_n$—COOEt; —CH2=CH—CN;
n is 1, 2 and 3;
comprising the step of:
i. mixing compound of formula (1a)

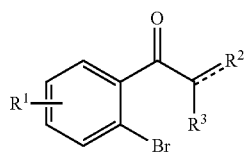

1

$R^1$ represents independently H, —OMe, —N—OH, halo, alkyl(C1-C5) and NR(2) wherein R is selected from the group consisting of H, O, alkyl(C1-C5) and aryl;

$R_2$ represents independently alkyl(C1-C5), aryl, —CN, —CO$_2$Et, vinyl(CH=CH$_2$);
R3 represents independently alkyl(C1-C5), vinyl;
with sodium azide in the ratio ranging between 1.2 to 1.5 eq. in the presence of 15 to 25 mol % copper catalyst, 15 to 25 mol % sodium ascorbate and 15 to 25 mol % L-proline, 1.5-2.0% of base and solvent followed by stirring to obtain compound of formula 2.

In an embodiment of the present invention, the reaction between formula 1a and sodium azide is taking place for a period in the range of 15 to 17 hr at temperature in the range of 60-100° C. to obtain compound of formula 2.

In an embodiment of the present invention, copper catalyst used is selected from the group consisting of CuSO$_4$.5H$_2$O, CuI, Cu$_2$O or Cu(OAc)$_2$.

In an embodiment of the present invention, copper catalyst used is CuSO$_4$. 5H$_2$O.

In another embodiment of the present invention, base used is selected from organic bases, or from inorganic bases either alone or in combination thereof.

In another embodiment of the present invention, organic base used is selected from the group consisting of pyridine, ethylamine, triethylamine (Et$_3$N), Triton B and TBAOH.

In another embodiment of the present invention, inorganic base used is selected from the group consisting of alkali or alkaline earth metal hydroxides, carbonates or bicarbonates.

In yet another embodiment of the present invention, solvent used is selected from the group consisting of DMSO, DMF, acetone, ethyl acetate and THF polyethylene glycol either alone or in combination thereof.

In yet another embodiment of the present invention, the yield of compound of Formula 2 is in the range of 50 to 65%.

In yet another embodiment of the present invention, said process is optionally carried out with compound of formula (3)

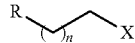

wherein X is a halide selected from Cl, Br, F or I,
R is alkyl
and n=0, 1 or 2
to obtain compound of formula 2.

In yet another embodiment of the present invention, the one pot $S_NAr$-Smalley cyclization of α,β-unsaturated ketones 1l-1n and β,γ-usaturated ketones 1o and 1p give exclusively 2-vinylindolin-3-one derivatives with >65% yields.

In yet another embodiment of the present invention, said compounds have fluorescing properties, with Stokes shift greater than 80.

DETAILED DESCRIPTION OF THE INVENTION

Figure 1:
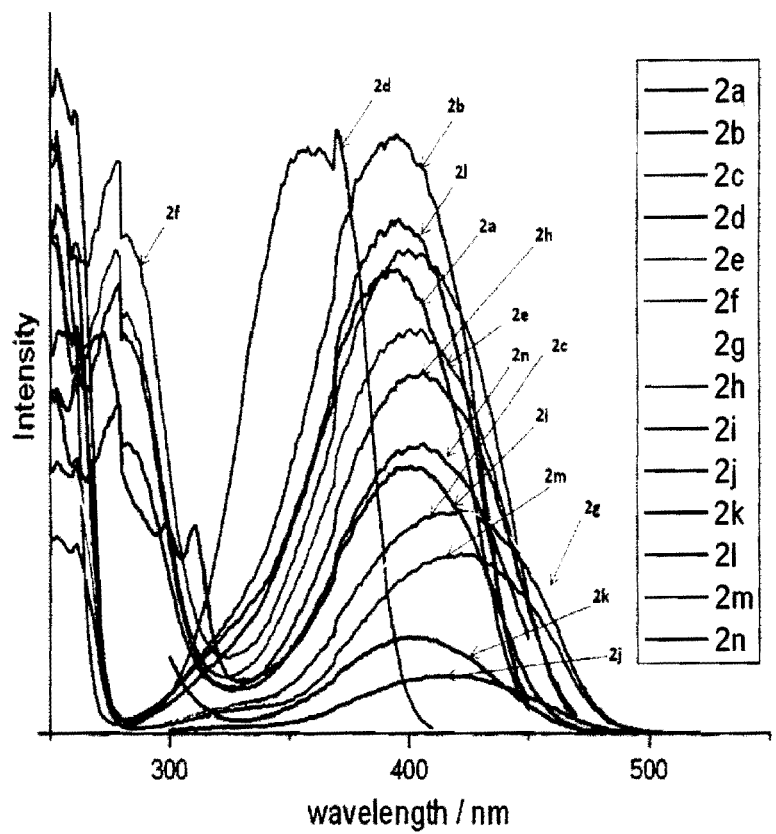
FIGS. 1(a) and (b) depict Absorption spectra and emission spectra of compounds 2a-2n respectively.
Figure 1B:
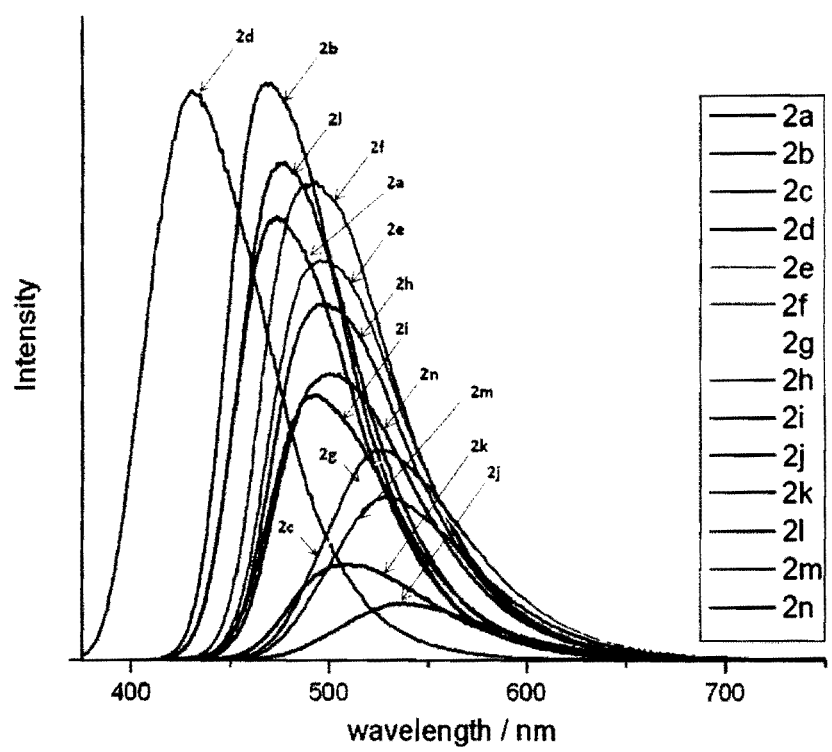
Figure 2:
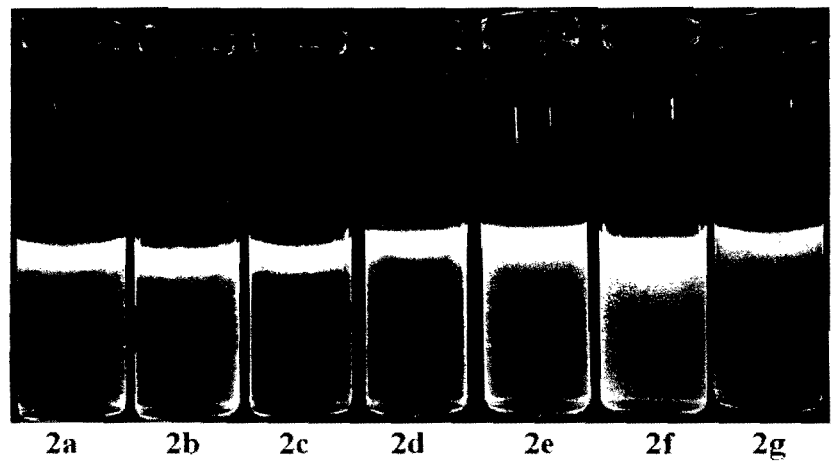
FIG. 2 depicts compounds 2a-2n in MeOH under 365 nm irradiation.
Figure 2:
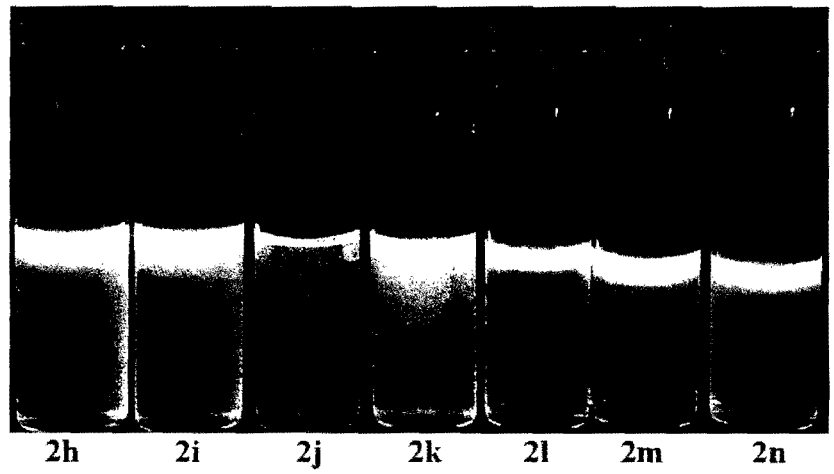

The present invention discloses cost effective, industrially feasible, one pot, copper catalysed $S_NAr$ and the Smalley rearrangement of α-halo phenyl sec-alkyl/sec alkenylketones to obtain 2,2-disubstituted 1,2-dihydro-3H-indol-3-one (trivially known as pseudo indoxyl) compounds of Formula 2 with Stokes shift greater than 80 and absorption in IR region which are useful as intermediate in the synthesis of many natural products and biologically active small molecules, find applications in the areas of fluorescence dyeing and in solar cell, Formula 2

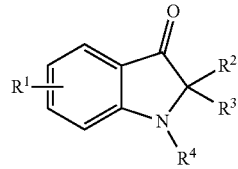

Wherein
$R^1$ represents independently H, —OMe, N—OH, halo, alkyl (C1-C5) and NR(2) wherein R is
selected from the group consisting of H, O, alkyl(C1-C5) and aryl;
$R_2$ represents independently alkyl(C1-C5), aryl, —CN, —CO$_2$Et, vinyl(CH=CH$_2$);
R3 represents independently alkyl(C1-C5), vinyl; or
R2 and R3 cyclize to form -CH2-(CH$_2$)$_n$—CH2— where n is 4, 5, 6;
R4 represents independently hydrogen, alkyl, —(CH$_2$)$_n$—Ar, —(CH$_2$)$_n$—CN, —(CH$_2$)$_n$—COOEt; —CH2=CH—CN;
n is 1, 2 and 3;
comprising the steps of:
i. mixing compound of formula (1a)

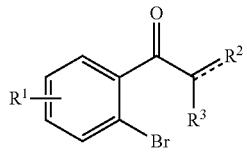

wherein
$R^1$ represents independently H, —OMe, —N—OH, halo, alkyl(C1-C5) and NR(2) wherein R is selected from the group consisting of H, O, alkyl(C1-C5) and aryl;
$R_2$ represents independently alkyl(C1-C5), aryl, —CN, —CO$_2$Et, vinyl(CH=CH$_2$);
R3 represents independently alkyl(C1-C5), vinyl;
with sodium azide in the ratio ranging between 1.2 to 1.5 eq. in the presence of 15 to 25 mol % copper catalyst, 15 to 25 mol % sodium ascorbate and 15 to 25 mol % L-proline, 1.5-2.0% of base and solvent followed by stirring for a period in the range of 15 to 17 hr at temperature in the range of 60-100° C. to obtain compound of formula 2.

In another aspect, the present invention provides one pot copper catalysed synthesis of pseudo indoxylcompounds of formula 2 employing orthobromophenyl sec-alkyl/sec-alkenyl ketones, which upon on reaction with sodium azide in the presence of copper salts, undergo sequential S$_N$Ar followed by Smalley cyclization, and optionally N-alkylation to obtain the desired product.

For identification of the optimum leaving group for the S$_N$Ar with azide as nucleophile, the screening of four α-halophenyl isopropyl ketones under the previously optimized conditions for the S$_N$Ar reactions with sodium azide revealed that the bromo-derivative is the better substrate. The reactions with the fluoro- and chloro substrates are found to be incomplete even after prolonged heating under the above-mentioned conditions. Along with the requisite S$_N$Ar-Smalley cyclization, the dehalogenation of the starting halo-derivative and also the in-situ reduction of the intermediate azide are observed to be competing reactions. The S$_N$Ar reaction with the iodo derivative is found to be facile. However, the corresponding dehalogenated derivative is isolated in substantial amounts. In case of bromo-derivative 1a, although the displacement reaction is slow, the required 2a is obtained as the main product in 65% yield. Control experiments employing substrate 1a revealed that the presence of the copper salt is essential.

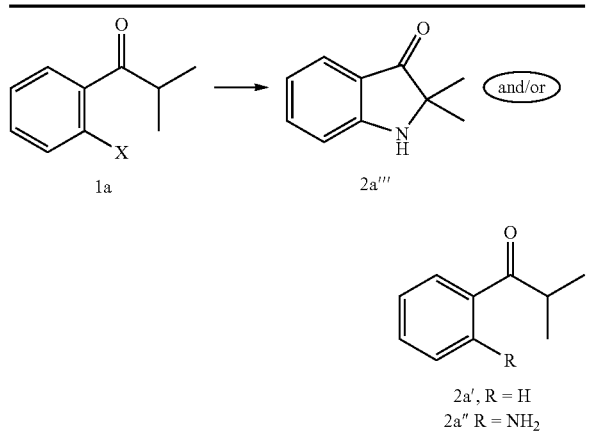

| X | 2a''' | 2a' | 2a'' |
|---|-------|-----|------|
| F | 29% | 18% | 31% |
| Cl | 16% | 21% | 27% |
| Br | 65% | 7% | 9% |
| I | 41% | 16% | 39% |

Conditions are as follow: NaN3 (1.5 eq.), CuSO4.5H2O (20 mol %) sodium ascorbate (20 mol %) and L-proline (20 mol %), K2CO3 (1.5 equiv). DMSO, 80° C., 12h.

Accordingly, the cost effective, industrially feasible, one pot process for the preparation of pseudoindoxyl compounds of Formula 2 with Stokes shift greater than 80 and absorption in IR region comprises sequential S$_N$Ar-Smalley cyclization of orthobromophenyl sec-alkyl/sec-alkenyl ketones (1a) with sodium azide in the presence of copper catalyst, sodium ascorbate (20 mol %) and L-proline (20 mol %), 1.5-2.0 equiv of base, and polar aprotic solvent to obtain compound of formula 2.

The process step is depicted in reaction scheme below:

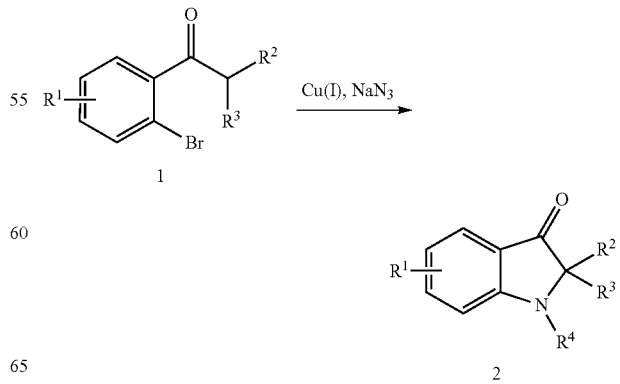

Wherein

R[1] represents independently H, —OMe, N—OH, halo, alkyl (C1-C5) and NR(2) wherein R is selected from the group consisting of H, O, alkyl(C1-C5) and aryl;

$R_2$ represents independently alkyl(C1-C5), aryl, —CN, —CO$_2$Et;

R3 represents independently alkyl(C1-C5), vinyl; or

R2 and R3 cyclize to form -CH2-(CH$_2$)$_n$—CH2— where n is 4, 5, 6;

R4 represents independently hydrogen, alkyl, —(CH$_2$)—Ar, —(CH$_2$)$_n$—CN, —(CH$_2$)—COOEt; —CH2=CH—CN;

n is 1, 2 and 3;

In another aspect, optionally N-alkylation is carried out in the presence of compound of formula 3

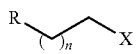

wherein X is a halide selected from Cl, Br, F or I and R is alkyl and n=0, 1 or 2.

Table 1 below discloses the following 2,2-disubstituted 1,2-dihydro-3H-indol-3-one (trivially known as pseudo indoxyl) compounds of Formula 2 prepared by the instant process:

TABLE 1

2a, 65%

2b, 71%

2c, 66%

2d, 68%

2e, 69%

TABLE 1-continued

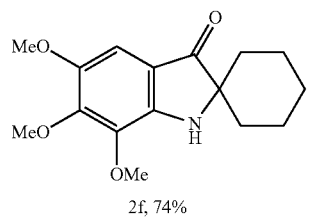 [SMILES: COc1cc2c(c(OC)c1OC)NC1(CCCCC1)C2=O]

2f, 74%

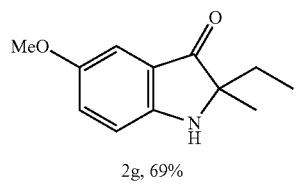

2g, 69%

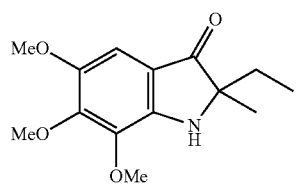

2h, 74%

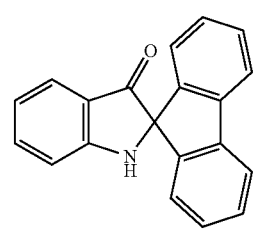

2i, 59%

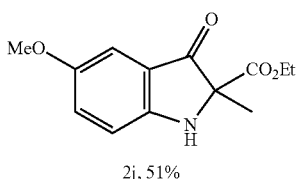

2j, 51%

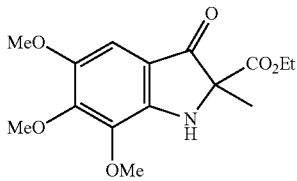

2k, 61%

The present invention discloses that the yields with the electron rich aryl derivatives are comparatively better than with the simple un-substituted benzene derivatives. The reaction is also compatible with the α-keto esters and resulted in the preparation of 3-oxoindoline-2-carboxylate; the main core of the Lipid Green dye (2j). The present invention disclose one pot S$_N$Ar-Smalley cyclization of α,β-unsaturated ketones 1l-1n and β,γ-usaturated ketones 1o and 1p to give exclusively 2-vinylindolin-3-one derivatives in very good yields. (Table 2)

TABLE 2
Synthesis of 2-vinylindolin-3-one derivatives
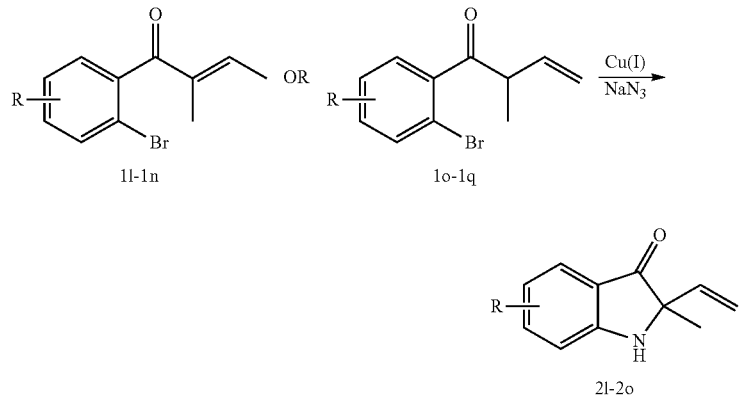
| Entry | Substrate | Product | Yield |
|---|---|---|---|
| 1 | 1l | 2l | 67% |
| 2 | 1m | 2m | 72% |
| 3 | 1n | 2n | 69% |
| 4 | 1o | 2m | 71% |
| 5 | 1p | 2n | 74% |

TABLE 2-continued

Synthesis of 2-vinylindolin-3-one derivatives

| Entry | Substrate | Product | Yield |
|---|---|---|---|
| 6 | 1q | 2o | 72% |

The 2,2-disubstituted 1,2-dihydro-3H-indol-3-one (trivially known as pseudo indoxyl) compounds of Formula 2 so formed are fluorescent in nature and their photo-physical properties were studied. In the 1,2-dihydroindol-3-one core structure, the amino group acts as a donor and the carbonyl group act as an acceptor which are connected via a benzene ring. The optical data reveals that the compounds with a methoxy group on the phenyl ring showed absorption and emission at longer wavelengths than those substrates having no substituent on the benzene ring or trimethoxy substituted benzene (Table 3).

TABLE 3

Optical properties of compounds 2a-2n

| Compound | $\lambda_{max}$ (nm)$^a$ | $\lambda_{em}$ (nm)$^a$ | Stokes shift (nm)$^b$ |
|---|---|---|---|
| 2a | 395 | 473 | 78 |
| 2b | 395 | 467 | 72 |
| 2c | 421 | 523 | 98 |
| 2d | 370 | 430 | 60 |
| 2e | 405 | 499 | 94 |
| 2f | 400 | 493 | 93 |
| 2g | 425 | 528 | 103 |
| 2h | 406 | 499 | 93 |
| 2i | 401 | 492 | 91 |
| 2j | 415 | 536 | 121 |
| 2k | 402 | 509 | 107 |
| 2l | 396 | 477 | 81 |
| 2m | 421 | 527 | 106 |
| 2n | 406 | 504 | 98 |
| 2o | 425 | 503 | 78 |

The data of Table 3 indicates that the —OMe group placed para to the amino group enhanced the donor capacity of the amino group and thereby shifted the peak to a longer wavelength. The presence of three —OMe groups on the benzene ring seems to decrease the acceptor ability of the carbonyl group. A similar trend is also noticed in the Stokes shifts (ranging from 70 nm-130 nm) displayed by these indol-3-ones. The indol-3-one (2j) having a single methoxy substituent on the aryl ring and a carboxylate group at $C_2$ displayed a large Stoke shift (121 nm).

EXAMPLES

The following examples are given by way of illustration and therefore should not be construed to limit the scope of the invention.

Experimental Methods

Reactions were carried out in anhydrous solvents under an atmosphere of argon in oven-dried glassware. Commercial reagents and solvents were used without purification. Column Chromatography was carried out by using spectrochem silica gel (60-120, 100-200, 230-400 mesh). 1H and 13C NMR spectroscopy measurements were carried out on Bruker AC 200 MHz or Bruker DRX 400 and Bruker DRX 500 MHz spectrometers, and TMS was used as an internal standard. 1H and 13C NMR chemical shifts are reported in ppm downfield from Chloroform-d ($\delta$=7.25) or TMS and coupling constants (J) are reported in Hertz (Hz). The following abbreviations are used to designate signal multiplicity: s=singlet, d=doublet, t=triplet, q=quartet, m=multiplet, b=broad. The multiplicity of 13C NMR signals was assigned with the help of DEPT spectra and the abbreviations used: s=singlet, d=doublet, t=triplet, q=quartet, represent C (quaternary), CH, CH2 and CH3 respectively. Mass spectroscopy was carried out on PI QStar Pulsar (Hybrid Quadrupole-TOF LC/MS/MS) and 4800 plus MALDI TOF/TOF Applied Biosystem spectrometer.

Comparative Example 1

Synthesis of Substrates 1a-1k

Compounds 1a and 1b were synthesized according to the reported procedure and the same was followed for the preparation of compounds 1c-1h. (L. Lunazzi, A. Mazzanti and M. Minzoni, *J. Org. Chem.*, 2006, 71, 9297; (b) T. J. Korn, M. A. Schade, M. N. Cheemala, S. Wirth, S. A. Guevara, G. Cahiez and P. Knochel, *Synthesis*, 2006, 3547).

Substrate 1i was prepared by acylation of fluorene in the presence of LDA (L. F. Tietze, T. Redert, H. P. Bell, S. Hellkamp and L. M. Levy, *Chem. Eur. J*, 2008, 14, 2527). Substrates 1j and 1k were prepared by following a sequence of Zn-mediated Reformatsky followed by the oxidation. (S. P. Chavan, S. Garai and U. R. Kalkote, *Tetrahedron*, 2012, 68, 8509).

Comparative Example 2

Synthesis of Substrate (1l to 1q)

S. K. Pandey and C. V. Ramana, *J Org. Chem.*, 2011, 76, 2315.

TABLE 4

Optimization of Reaction Condition with various Cu-catalysts

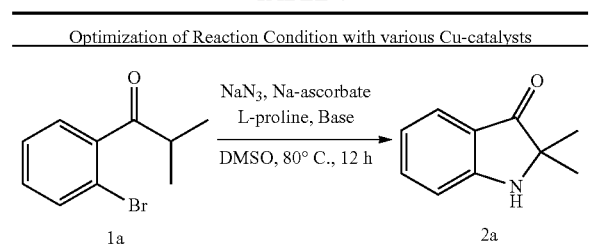

| Entry[a] | Cu-catalyst | Base | Isolated Yield |
|---|---|---|---|
| 1 | CuSO$_4$ 5H$_2$O | K$_2$CO$_3$ | 65% |
| 2 | CuSO$_4$ 5H$_2$O | KOH | 23% |
| 3 | CuSO$_4$ 5H$_2$O | Cs$_2$CO$_3$ | 57% |
| 4 | CuSO$_4$ 5H$_2$O | Triton B | 59% |
| 5 | CuSO$_4$ 5H$_2$O | TBAOH | 51% |

Scheme.

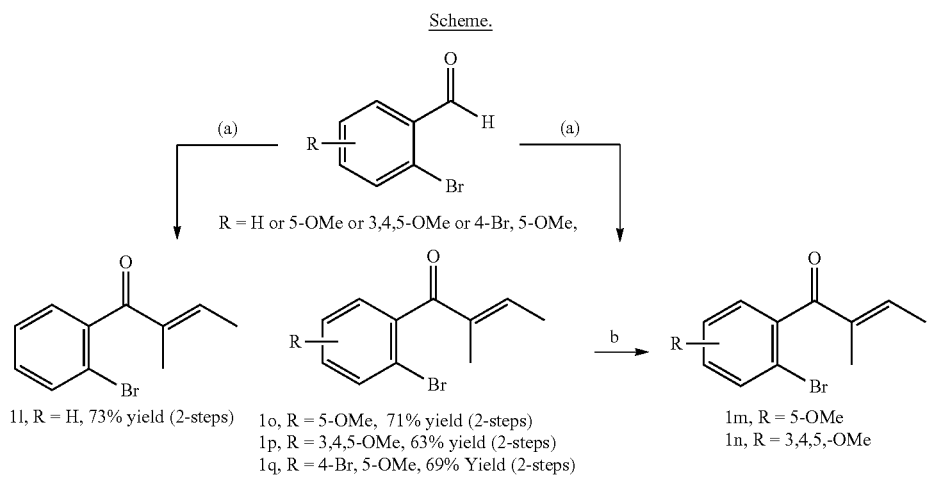

Reagents and conditions: a) (i) crotyl bromide, Zn, THF, 0° C. to rt; (ii) IBX, EtOAc, reflux, 3-4 h; b) DBU, DCM, 5 m.

To a vigorously stirred suspension of Zn (5.0 eq.) and propargyl bromide (3.0 eq.) in THF (10 mL) was added a solution of aldehyde (1.0 eq.) in THF (10 mL) and the stirring was continued for another 30 min. The reaction mixture was cooled to 0° C., sat. NH4Cl (10 mL) was added drop wise for 30 min and stirring was continued for additional 2 h. Reaction mixture was filtered through celite pad and the solvent was evaporated under vacuum. The crude mixtures dilute with water and extracted with ethyl acetate (3×25 ml), washed with brine, dried (Na2SO4), and concentrated. The crude residue was used for next step without further purification.

At 27° C., a solution of the above crude alcohol in ethyl acetate (10 mL) was treated with IBX (1.3 eq.) stirred at reflux temperature for 3 h. After complete consumption of starting material, the reaction mixture was cooled to r.t 27° C. and filtered through a celite pad. Solvent was evaporated under reduced pressure and the crude residue was purified over silica gel column (ethyl acetate and pet ether as eluent) to obtain the keto compounds (1l, 1o and 1p) in 60-80% yields over two steps. Compound 1o and 1p have been stirred with DBU in CH$_2$Cl$_2$ for 5 min to afford the required 1m and 1n respectively in quantitative yields.

TABLE 4-continued

Optimization of Reaction Condition with various Cu-catalysts

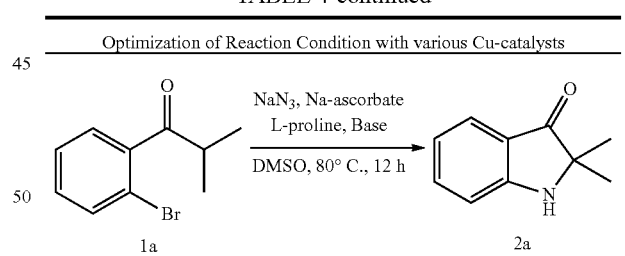

| Entry[a] | Cu-catalyst | Base | Isolated Yield |
|---|---|---|---|
| 6 | CuSO$_4$ 5H$_2$O | Et$_3$N | 41% |
| 7 | CuSO$_4$ 5H$_2$O | — | 33% |
| 8 | CuI | K$_2$CO$_3$ | 36% |
| 9 | CuI | KOH | 61% |
| 10 | CuI | — | 46%[b] |
| 11 | CuI | — | 36% |
| 12 | CuI | — | 53%[b,c] |
| 13 | Cu$_2$O | K$_2$CO$_3$ | 36%[b] |
| 14 | Cu(OAc)$_2$ | K$_2$CO$_3$ | 43% |

[a]Reaction Parameter: 1.2 eq NaN$_3$; 20 mol % L-proline, Na-ascorbate, Cu-cat in DMSO;
[b]reaction did without Na-ascorbate.
[c]PEG used as a solvent.

Example 1

2,2-Dimethylindolin-3-one (2a)

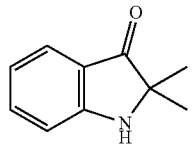

To a solution of 1-(2-bromophenyl)-2-methylpropan-1-one (0.1 g, 4.4 mmol) in DMSO, were added L-proline (10.14 mg, 0.88 mmol), $K_2CO_3$ (91.95 mg, 6.60 mmol), $CuSO_4$:$5H_2O$ (21.99 mg, 0.88 mmol), sodium ascorbate (17.45 mg, 0.88 mmol), and $NaN_3$ (34.35 mg, 2.28 mmol). The mixture was stirred for 16 h at 70° C. (oil bath temperature). The reaction mixture was diluted with 30 mL of water and extracted with ethyl acetate (3×30 mL). Combined organic layer was dried ($Na_2SO_4$) and evaporated under reduced pressure. The crude was purified over silica gel (ethyl acetate and pet ether as eluent) to procure 2a (0.046 g, 2.85 mmol) in 65% yields.

Brown solid; 65% yield; Rf=0.4 (10% ethyl acetate/pet. ether); mp: 81-82° C.; IR (Nujol)v: 3363, 2924, 2855, 1681, 1619, 1464, 1375, 1142, 993, 760, 648 cm-1; 1H NMR (200 MHz, CDCl3): □ 1.31 (s, 6H), 4.69 (s, 1H), 6.75-6.84 (m, 2H), 7.43 (ddd, J=1.4, 7.1, 8.4 Hz, 1H), 7.60 (dt, J=1.0, 7.7 Hz, 1H); 13C NMR (50 MHz, CDCl3): □24.4 (q, 2C), 63.9 (s), 112.5 (d), 118.7 (d), 119.5 (s), 125.0 (d), 137.2 (d), 159.6 (s), 205.2 (s) ppm; ESI-MS: 162.10 (65%, [M+H]+); HRMS (ESI+): calcd. for C10H11NOH+ 162.0913, found 162.0913.

Example 2

Spiro[cyclohexane-1,2'-indolin]-3'-one (2b)

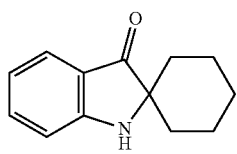 [SMILES: O=C1c2ccccc2NC12CCCCC2]

To a solution of (2-bromophenyl)(cyclohexyl)methanone (0.1 g, 3.74 mmol) in DMSO, were added L-proline (8.62 mg, 0.74 mmol), $K_2CO_3$ (77.59 mg, 5.61 mmol), $CuSO_4$:$5H_2O$ (18.69 mg, 0.74 mmol), sodium ascorbate (14.83 mg, 0.74 mmol), and $NaN_3$ (29.20 mg, 4.49 mmol). The mixture was stirred for 16 h at 70° C. (oil bath temperature). The reaction mixture was diluted with 30 mL of water and extracted with ethyl acetate (3×30 mL). Combined organic layer was dried ($Na_2SO_4$) and evaporated under reduced pressure. The crude was purified over silica gel (ethyl acetate and pet ether as eluent) to procure 2b (0.054 g, 2.68 mmol) in 71% yields.

Yellow solid; 71% yield; $R_f$=0.5 (10% ethyl acetate/pet. ether); mp: 133-134° C.; IR (Nujol)v: 3330, 2924, 2854, 1669, 1620, 1463, 1377, 1141, 971, 751, 664 cm$^{-1}$; $^1$H NMR (200 MHz, CDCl$_3$): □1.34-1.54 (m, 5H), 1.68-1.91 (m, 5H), 5.04 (s, 1H), 6.79 (dt, J=0.8, 7.8 Hz, 1H), 6.86 (br d, J=8.3 Hz, 1H), 7.42 (ddd, J=1.3, 7.1, 8.4 Hz, 1H), 7.60 (br d, J=7.8 Hz, 1H); $^{13}$C NMR (50 MHz, CDCl$_3$): □22.5 (t, 2C), 24.8 (t), 32.8 (t, 2C), 66.9 (s), 112.6 (d), 118.8 (d), 120.4 (s), 125.0 (d), 137.0 (d), 159.9 (s), 204.9 (s) ppm; ESI-MS (m/z): 202.05 (100%, [M+H]), 224.01 (30%, [M+Na]$^+$); HRMS (ESI+): calcd. for $C_{13}H_{15}NOH^+$ 202.1226. found 202.1226.

Example 3

5-Methoxy-2,2-dimethylindolin-3-one (2c)

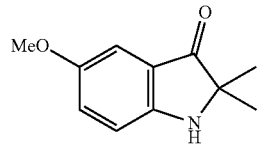

To a solution of 1-(2-bromo-5-methoxyphenyl)-2-methylpropan-1-one (0.1 g, 3.88 mmol) in DMSO, were added L-proline (8.96 mg, 0.77 mmol), $K_2CO_3$ (80.62 mg, 5.83 mmol), $CuSO_4$:$5H_2O$ (19.42 mg, 0.77 mmol), sodium ascorbate (15.41 mg, 0.77 mmol), and $NaN_3$ (30.34 mg, 4.66 mmol). The mixture was stirred for 15 h at 70° C. (oil bath temperature). The reaction mixture was diluted with 30 mL of water and extracted with ethyl acetate (3×30 mL). Combined organic layer was dried ($Na_2SO_4$) and evaporated under reduced pressure. The crude was purified over silica gel (ethyl acetate and pet ether as eluent) to procure 2c (0.049 g, 2.56 mmol) in 66% yields.

Brown solid; 66% yield; Rf=0.2 (10% ethyl acetate/pet. ether); mp: 56-57° C.; IR (Nujol)v: 3324, 2924, 2854, 1679, 1494, 1462, 1376, 1234, 1139, 1029, 913, 793 cm-1; 1H NMR (200 MHz, CDCl3): □ 1.32 (s, 6H), 3.76 (s, 3H), 4.30 (s, 1H), 6.81 (dd, J=0.5, 8.8 Hz, 1H), 7.04 (d, J=2.6 Hz, 1H), 7.14 (dd, J=2.7, 8.8 Hz, 1H); 13C NMR (50 MHz, CDCl3): □24.6 (q, 2C), 55.8 (q), 64.9 (s), 104.7 (d), 114.3 (d), 120.0 (s), 127.8 (d), 153.4 (s), 155.4 (s), 205.5 (s) ppm; ESI-MS (m/z): 190.07 (100%, [M−H]+), 192.10 (25%, [M+H]+); HRMS (ESI+): calcd. for C11H13NO2H+ 192.1019, found 192.1019.

Example 4

5'-Methoxyspiro[cyclohexane-1,2'-indolin]-3'-one (2d)

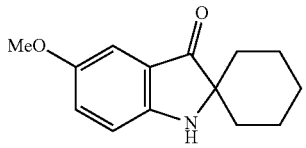 [SMILES: COc1ccc2c(c1)C(=O)C1(CCCCC1)N2]

To a solution of (2-bromo-5-methoxyphenyl)(cyclohexyl)methanone (0.1 g, 3.36 mmol) in DMSO, were added L-proline (7.75 mg, 0.67 mmol), $K_2CO_3$ (69.76 mg, 5.04 mmol), $CuSO_4$:$5H_2O$ (16.8 mg, 0.67 mmol), sodium ascorbate (13.33 mg, 0.67 mmol), and $NaN_3$ (26.25 mg, 4.03 mmol). The mixture was stirred for 17 h at 70° C. (oil bath temperature). The reaction mixture was diluted with 30 mL of water and extracted with ethyl acetate (3×30 mL). Combined organic layer was dried ($Na_2SO_4$) and evaporated under reduced pressure. The crude was purified over silica gel (ethyl acetate and pet ether as eluent) to procure 2d (0.053 g, 2.29 mmol) in 68% yields.

Yellow solid; 68% yield; Rf=0.3 (15% ethyl acetate/pet. ether); mp: 63-64° C.; IR (CHCl3)v: 3404, 2925, 1714, 1601, 1489, 1460, 1377, 1269, 1217, 1118, 1029, 946, 811, 765, 721 cm-1; 1H NMR (200 MHz, CDCl3): ☐ 1.35-1.50 (m, 5H), 1.68-1.85 (m, 5H), 3.75 (s, 3H), 4.71 (s, 1H), 6.84 (d, J=8.7 Hz, 1H), 7.04 (d, J=2.6 Hz, 1H), 7.13 (dd, J=2.7, 8.8, 1H); 13C NMR (50 MHz, CDCl3): ☐21.7 (t, 2C), 24.6 (t), 31.7 (t, 2C), 55.9 (s), 90.4 (s), 104.3 (d), 114.6 (d), 120.0 (s), 128.1 (d), 154.6 (s), 166.6 (s), 204.5 (s) ppm; ESI-MS (m/z): 230.05 (100%, [M−H]+), 232.09 (45%, [M+H]+); HRMS (ESI+): calcd. for C14H17NO2H+ 232.1332, found 232.1331.

Example 5

5,6,7-Trimethoxy-2,2-dimethylindolin-3-one (2e)

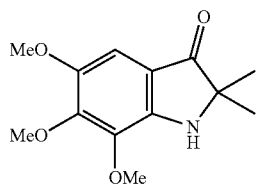 [SMILES: COc1cc2c(c(OC)c1OC)NC(C)(C)C2=O]

To a solution of 1-(2-bromo-3,4,5-trimethoxyphenyl)-2-methylpropan-1-one (0.1 g, 3.15 mmol) in DMSO, were added L-proline (7.26 mg, 0.63 mmol), K$_2$CO$_3$ (65.36 mg, 4.72 mmol), CuSO$_4$:5H$_2$O (15.74 mg, 0.63 mmol), sodium ascorbate (12.49 mg, 0.63 mmol), and NaN$_3$ (24.60 mg, 3.78 mmol). The mixture was stirred for 13 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2e (0.055 g, 2.18 mmol) in 69% yields.

Yellow solid; 69% yield; R$_f$=0.3 (20% ethyl acetate/pet. ether); mp: 74-75° C.; IR (Nujol)v: 3360, 2854, 1704, 1617, 1459, 1376, 1297, 1133, 975, 722 cm$^{-1}$; $^1$H NMR (200 MHz, CDCl$_3$): ☐ 1.32 (s, 6H), 3.81 (s, 3H), 3.93 (s, 3H), 3.96 (s, 3H), 4.42 (s, 1H), 6.85 (s, 1H); $^{13}$C NMR (50 MHz, CDCl$_3$): ☐24.9 (q, 2C), 56.3 (q), 60.5 (q), 61.1 (q), 64.6 (s), 100.2 (d), 114.1 (s), 139.0 (s), 148.0 (s), 149.9 (s), 150.4 (s), 204.3 (s) ppm; ESI-MS: 252.07 (75%, [M+H]$^+$), 273.96 (55%, [M+Na]$^+$); HRMS (ESI+): calcd. for C$_{13}$H$_{17}$NO$_4$H$^+$ 252.1230, found 252.1227.

Example 6

5',6',7'-Trimethoxyspiro[cyclohexane-1,2'-indolin]-3'-one (2f)

To a solution of (2-bromo-3,4,5-trimethoxyphenyl)(cyclohexyl)methanone (0.1 g, 2.79 mmol) in DMSO, were added L-proline (6.45 mg, 0.56 mmol), K$_2$CO$_3$ (58.03 mg, 4.19 mmol), CuSO$_4$:5H$_2$O (13.98 mg, 0.56 mmol), sodium ascorbate (11.09 mg, 0.56 mmol), and NaN$_3$ (21.84 mg, 3.35 mmol). The mixture was stirred for 16 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2f (0.061 g, 2.09 mmol) in 74% yields.

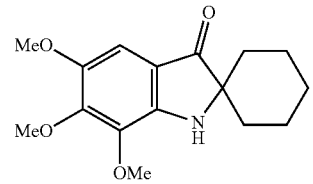 [SMILES: COc1cc2c(c(OC)c1OC)NC1(CCCCC1)C2=O]

Brown solid; 74% yield; R$_f$=0.4 (20% ethyl acetate/pet. ether); mp: 122-123° C.; IR (Nujol)v: 3283, 2923, 1659, 1621, 1459, 1376, 1310, 1252, 1102, 1042, 964, 898, 783 cm$^{-1}$; $^1$H NMR (200 MHz, CDCl$_3$): ☐ 1.37-1.50 (m, 5H), 1.72-1.89 (m, 5H), 3.80 (s, 3H), 3.96 (s, 6H), 4.76 (s, 1H), 6.84 (s, 1H); $^{13}$C NMR (50 MHz, CDCl$_3$): ☐22.6 (t, 2C), 24.7 (t), 32.9 (t, 2C), 56.2 (q), 60.5 (q), 61.1 (q), 67.6 (s), 100.0 (d), 114.9 (s), 139.0 (s), 147.9 (s), 149.6 (s), 150.6 (s), 204.1 (s) ppm; ESI-MS: 292.17 (35%, [M+H]$^+$), 314.03 (65%, [M+Na]$^+$); HRMS (ESI+): calcd. for C$_{16}$H$_{21}$NO$_4$H$^+$ 292.1543, found 292.1544.

Example 7

2-Ethyl-5-methoxy-2-methylindolin-3-one (2g)

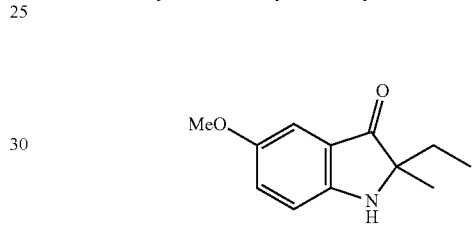

To a solution of 1-(2-bromo-5-methoxyphenyl)-2-methylbutan-1-one (0.1 g, 3.68 mmol) in DMSO, were added L-proline (8.49 mg, 0.73 mmol), K$_2$CO$_3$ (76.42 mg, 5.53 mmol), CuSO$_4$:5H$_2$O (14.61 mg, 0.73 mmol), sodium ascorbate (14.61 mg, 0.73 mmol), and NaN$_3$ (28.77 mg, 4.42 mmol). The mixture was stirred for 17 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2g (0.053 g, 2.58 mmol) in 69% yields.

Yellow solid; 69% yield; R$_f$=0.3 (15% ethyl acetate/pet. ether); mp: 76-77° C.; IR (CHCl$_3$)v: 3341, 2967, 2927, 1670, 1496, 1455, 1262, 1228, 1140, 1029, 821, 788 cm$^{-1}$; $^1$H NMR (200 MHz, CDCl$_3$): ☐70.79 (t, J=7.5 Hz, 3H), 1.2 (s, 3H), 1.66 (dq, J=7.3, 14.0 Hz, 1H), 1.73 (dq, J=7.5, 14.9 Hz, 1H), 3.75 (s, 3H), 4.27 (s, 1H), 6.82 (d, J=8.8 Hz, 1H), 7.02 (d, J=2.6 Hz, 1H), 7.12 (dd, J=2.7, 8.7 Hz, 1H); $^{13}$C NMR (50 MHz, CDCl$_3$): ☐8.1 (q), 23.1 (q), 31.0 (t), 55.7 (q), 68.3 (s), 104.4 (d), 114.1 (d), 120.9 (s), 127.8 (d), 153.2 (s), 156.2 (s), 205.6 (s) ppm; ESI-MS: 203.97 (100%, [M−H]$^+$), 205.97 (25%, [M+H]$^+$); HRMS (ESI+): calcd. for C$_{12}$H$_{15}$NO$_2$H$^+$ 206.1176, found 206.1174.

Example 8

2-Ethyl-5,6,7-trimethoxy-2-methylindolin-3-one (2h)

To a solution of 1-(2-bromo-5-methoxyphenyl)-2-methylbutan-1-one (0.1 g, 3.68 mmol) in DMSO, were added L-proline (8.49 mg, 0.73 mmol), K$_2$CO$_3$ (76.42 mg, 5.53 mmol), CuSO$_4$:5H$_2$O (14.61 mg, 0.73 mmol), sodium ascorbate (14.61 mg, 0.73 mmol), and NaN$_3$ (28.77 mg, 4.42 mmol). The mixture was stirred for 17 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2g (0.053 g, 2.58 mmol) in 69% yields.

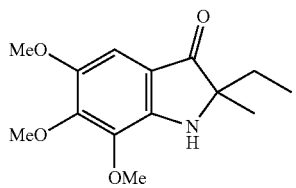 [SMILES: CCC1(C)Nc2c(cc(OC)c(OC)c2OC)C1=O]

Yellow liquid; 72% yield; R$_f$=0.3 (20% ethyl acetate/pet. ether); IR (CHCl$_3$)v: 3344, 2967, 1676, 1618, 1501, 1469, 1370, 1301, 1134, 1091, 1002, 959, 792 cm$^{-1}$; $^1$H NMR (200 MHz, CDCl$_3$): □ 0.78 (t, J=7.4 Hz, 3H), 1.27 (s, 3H), 1.66 (dq, J=7.3, 14.1 Hz, 1H), 1.73 (dq, J=7.5, 14.9 Hz, 1H), 3.79 (s, 3H), 3.92 (s, 3H), 3.96 (s, 3H) 4.38 (s, 1H), 6.82 (s, 1H); $^{13}$C NMR (50 MHz, CDCl$_3$): □8.1 (q), 23.2 (q), 31.0 (t), 56.2 (q), 60.5 (q), 61.1 (q), 67.9 (s), 100.0 (d), 115.1 (s), 138.8 (s), 147.8 (s), 149.8 (s), 151.0 (s), 204.3 (s) ppm; ESI-MS: 266.01 (100%, [M+H]$^+$), 288.03 (35%, [M+Na]$^+$); HRMS (ESI+): calcd. for C$_{14}$H$_{19}$NO$_4$H$^+$ 266.1387, found 266.1385.

Example 9

Spiro[fluorene-9,2'-indolin]-3'-one (2i)

To a solution of (2-bromophenyl)(9H-fluoren-9-yl)methanone (0.1 g, 2.86 mmol) in DMSO, were added L-proline (6.59 mg, 0.57 mmol), K$_2$CO$_3$ (59.36 mg, 4.29 mmol), CuSO$_4$:5H$_2$O (14.30 mg, 0.57 mmol), sodium ascorbate (11.35 mg, 0.57 mmol), and NaN$_3$ (22.34 mg, 3.43 mmol). The mixture was stirred for 18 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2i (0.048 g, 1.69 mmol) in 59% yields.

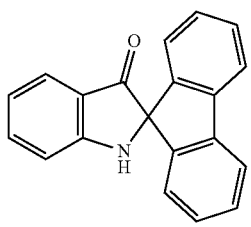 [SMILES: O=C1c2ccccc2NC12c1ccccc1-c1ccccc12]

Yellow solid; 59% yield; R$_f$=0.3 (20% ethyl acetate/pet. ether); mp: 211-212° C.; IR (Nujol)v: 3386, 2924, 1699, 1614, 1463, 1377, 1152, 1028, 748, 736, 649 cm$^{-1}$; $^1$H NMR (400 MHz, CDCl$_3$): □4.91 (s, 1H), 6.90 (t, J=7.4 Hz, 1H), 7.01 (d, J=8.3 Hz, 1H), 7.15-7.24 (m, 4H), 7.38 (dt, J=1.2, 7.5 Hz, 2H), 7.54 (br t, J=7.6 Hz, 1H), 7.66 (d, J=7.8 Hz, 1H), 7.71 (d, J=7.6 Hz, 2H); $^{13}$C NMR (100 MHz, CDCl$_3$): □77.7 (s), 112.6 (d), 119.4 (d), 120.6 (d, 2C), 120.7 (s), 122.9 (d, 2C), 125.9 (d), 128.0 (d, 2C), 129.3 (d, 2C), 137.5 (d), 141.8 (s, 2C), 143.5 (s, 2C), 161.9 (s), 199.2 (s) ppm; ESI-MS (m/z): 283.97 (100%, [M+H]$^+$), 305.94 (90%, [M+Na]$^+$); HRMS (ESI+): calcd. for C$_{20}$H$_{13}$NOH$^+$ 284.1070, found 284.1071.

Example 10

Ethyl 5-methoxy-2-methyl-3-oxoindoline-2-carboxylate (2j)

To a solution of ethyl 3-(2-bromo-5-methoxyphenyl)-2-methyl-3-oxopropanoate (0.1 g, 3.17 mmol) in DMSO, were added L-proline (7.31 mg, 0.63 mmol), K$_2$CO$_3$ (65.78 mg, 4.75 mmol), CuSO$_4$:5H$_2$O (15.84 mg, 0.63 mmol), sodium ascorbate (12.57 mg, 0.63 mmol), and NaN$_3$ (24.75 mg, 3.80 mmol). The mixture was stirred for 18 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2j (0.041 g, 1.64 mmol) in 51% yields.

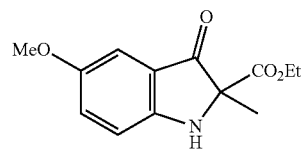 [SMILES: CCOC(=O)C1(C)Nc2ccc(OC)cc2C1=O]

Yellow liquid; 51% yield; Rf=0.3 (25% ethyl acetate/pet. ether); IR (CHCl3)v: 3385, 2700, 2400, 1703, 1495, 1219, 1108, 933, 771 cm-1; 1H NMR (400 MHz, CDCl3): □1.27 (t, J=7.2 Hz, 3H), 1.63 (s, 3H), 3.76 (s, 3H), 4.14-4.28 (m, 2H), 4.95 (s, 1H), 6.93 (br d, J=8.9 Hz, 1H), 7.03 (d, J=2.7 Hz, 1H), 7.17 (dd, J=2.8, 8.9 Hz, 1H); 13C NMR (100 MHz, CDCl3): □14.1 (q), 22.1 (q), 55.8 (q), 62.6 (t), 71.5 (s), 104.9 (d), 115.1 (d), 120.2 (s), 128.1 (d), 154.4 (s), 156.9 (s), 169.4 (s), 196.8 (s) ppm; ESI-MS (m/z): 271.97 (100%, [M+Na]+); HRMS (ESI+): calcd. for C13H15NO4H+ 250.1074, found 250.1073.

Example 11

Ethyl 5,6,7-trimethoxy-2-methyl-3-oxoindoline-2-carboxylate (2k)

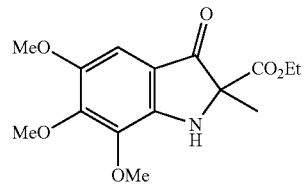 [SMILES: CCOC(=O)C1(C)Nc2c(cc(OC)c(OC)c2OC)C1=O]

To a solution of ethyl 3-(2-bromo-3,4,5-trimethoxyphenyl)-2-methyl-3-oxopropanoate (0.1 g, 2.66 mmol) in DMSO, were added L-proline (6.14 mg, 0.53 mmol), K$_2$CO$_3$ (55.25 mg, 3.99 mmol), CuSO$_4$:5H$_2$O (13.31 mg, 0.53 mmol), sodium ascorbate (10.56 mg, 0.53 mmol), and NaN$_3$ (20.79 mg, 3.19 mmol). The mixture was stirred for 15 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2k (0.050 g, 1.61 mmol) in 61% yields.

Yellow liquid; 61% yield; Rf=0.2 (25% ethyl acetate/pet. ether); IR (CHCl3)ν: 3356, 2932, 1741, 1697, 1499, 1469, 1369, 1297, 1091, 931, 756 cm-1; 1H NMR (200 MHz, CDCl3): ☐ 1.26 (br t, J=7.1 Hz, 3H), 1.63 (s, 3H), 3.81 (s, 3H), 3.95 (s, 3H), 3.99 (s, 3H), 5.02 (s, 1H), 6.83 (s, 1H); 13C NMR (100 MHz, CDCl3): ☐ 14.1 (q), 21.9 (q), 56.3 (q), 60.7 (q), 61.2 (q), 62.5 (t), 71.1 (s), 100.4 (d), 114.2 (s), 139.4 (s), 148.9 (s), 150.3 (s), 151.9 (s), 169.4 (s), 195.6 (s) ppm; ESI-MS: 332.03 (100%, [M+Na]+); HRMS (ESI+): calcd. for C15H19NO6H+ 310.1285, found 310.1285.

Example 12

2-Methyl-2-vinylindolin-3-one (2l)

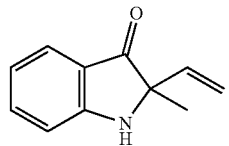

To a solution of (E)-1-(2-bromophenyl)-2-methylbut-2-en-1-one (0.1 g, 4.18 mmol) in DMSO, were added L-proline (9.63 mg, 0.83 mmol), K$_2$CO$_3$ (86.70 mg, 6.27 mmol), CuSO$_4$:5H$_2$O (20.88 mg, 0.83 mmol), sodium ascorbate (16.57 mg, 0.83 mmol), and NaN$_3$ (32.63 mg, 5.01 mmol). The mixture was stirred for 16 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2l (0.049 g, 2.82 mmol) in 67% yields.

Yellow liquid; 67% yield; Rf=0.3 (10% ethyl acetate/pet. ether); IR (CHCl3)ν: 3346, 2973, 2926, 1682, 1620, 1470, 1324, 1133, 1099, 969, 752, 702 cm-1; 1H NMR (200 MHz, CDCl3): ☐ 1.44 (s, 3H), 4.72 (s, 1H), 5.14 (dd, J=0.8, 10.4 Hz, 1H), 5.34 (dd, J=0.8, 17.2 Hz, 1H), 5.88 (dd, J=10.4, 17.2 Hz, 1H), 6.77-6.89 (m, 2H), 7.45 (ddd, J=1.3, 7.1, 8.4 Hz, 1H) 7.58 (br d, J=7.8 Hz, 1H); 13C NMR (50 MHz, CDCl3): ☐ 22.8 (q), 68.3 (s), 112.4 (d), 114.5 (t), 119.0 (d), 119.3 (s), 125.3 (d), 137.3 (d), 137.5 (d), 159.8 (s), 202.0 (s) ppm; ESI-MS: 174.01 (40%, [M+H]+); HRMS (ESI+): calcd. for C11H11NOH+ 174.0913, found 174.0913.

Example 13

5-Methoxy-2-methyl-2-vinylindolin-3-one (2m)

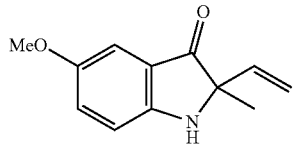

To a solution of 1-(2-bromo-5-methoxyphenyl)-2-methylbut-3-en-1-one OR (E)-1-(2-bromo-5-methoxyphenyl)-2-methylbut-2-en-1-one (0.1 g, 3.71 mmol) in DMSO, were added L-proline (8.56 mg, 0.74 mmol), K$_2$CO$_3$ (77.03 mg, 5.57 mmol), CuSO$_4$:5H$_2$O (18.55 mg, 0.74 mmol), sodium ascorbate (14.72 mg, 0.74 mmol), and NaN$_3$ (28.99 mg, 4.45 mmol). The mixture was stirred for 15 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2m (0.054 g, 2.65 mmol) in 71% yields.

Yellow liquid; 71% yield; Rf=0.4 (15% ethyl acetate/pet. ether); IR (CHCl3)ν: 3346, 2927, 1681, 1495, 1440, 1270, 1227, 1125, 1028, 924, 821, 783 cm-1; 1H NMR (200 MHz, CDCl3): ☐ 1.44 (s, 3H), 3.75 (s, 3H), 4.41 (s, 1H), 5.14 (dd, J=0.8, 10.3 Hz, 1H), 5.34 (dd, J=0.8, 17.2 Hz, 1H), 5.87 (dd, J=10.4, 17.24 Hz, 1H), 6.85 (dd, J=0.4, 8.8 Hz, 1H), 7.02 (d, J=2.6 Hz, 1H), 7.14 (dd, J=2.7, 8.8 Hz, 1H); 13C NMR (50 MHz, CDCl3): ☐ 22.8 (q), 55.8 (q), 69.3 (s), 105.0 (d), 114.2 (d), 114.5 (t), 119.7 (s), 127.9 (d), 137.7 (d), 153.6 (s), 155.6 (s), 202.3 (s) ppm; ESI-MS: 204.02 (100%, [M+H]+); HRMS (ESI+): calcd. for C12H13NO2H+ 204.1019, found 204.1019.

Example 14

5,6,7-Trimethoxy-2-methyl-2-vinylindolin-3-one (2n)

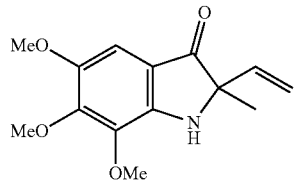 [SMILES: C=CC1(C)Nc2c(cc(OC)c(OC)c2OC)C1=O]

To a solution of 1-(2-bromo-3,4,5-trimethoxyphenyl)-2-methylbut-3-en-1-one OR (E)-1-(2-bromo-3,4,5-trimethoxyphenyl)-2-methylbut-2-en-1-one (0.1 g, 3.03 mmol) in DMSO, were added L-proline (6.99 mg, 0.61 mmol), K$_2$CO$_3$ (62.97 mg, 4.55 mmol), CuSO$_4$:5H$_2$O (15.17 mg, 0.61 mmol), sodium ascorbate (12.04 mg, 0.61 mmol), and NaN$_3$ (23.70 mg, 3.64 mmol). The mixture was stirred for 16 h at 70° C. (oil bath temperature). The reaction mixture was diluted with 30 mL of water and extracted with ethyl acetate (3×30 mL). Combined organic layer was dried (Na$_2$SO$_4$) and evaporated under reduced pressure. The crude was purified over silica gel (ethyl acetate and pet ether as eluent) to procure 2n (0.059 g, 2.24 mmol) in 74% yields.

Yellow liquid; 74% yield; Rf=0.3 (25% ethyl acetate/pet. ether); IR (CHCl3)ν: 3344, 2932, 1684, 1618, 1500, 1469, 1304, 1123, 1090, 926, 790 cm-1; 1H NMR (400 MHz, CDCl3): ☐ 1.44 (s, 3H), 3.80 (s, 3H), 3.95 (s, 3H), 3.98 (s, 3H), 4.53 (s, 1H), 5.14 (br d, J=10.5 Hz, 1H), 5.34 (br d, J=17.2 Hz, 1H), 5.87 (dd, J=10.5, 17.2 Hz, 1H), 6.83 (s, 1H); 13C NMR (100 MHz, CDCl3): ☐22.8 (q), 56.3 (q), 60.6 (q), 61.2 (q), 68.9 (s), 100.5 (d), 113.8 (s), 114.3 (t), 137.8 (d), 138.9 (s), 148.1 (s), 150.0 (s), 150.6 (s), 201.1 (s) ppm; ESI-MS (m/z): 263.88 (100%, [M+H]+), 285.99 (30%, [M+Na]+); HRMS (ESI+): calcd. for C14H17NO4H+ 264.1230, found 264.1230.

Example 15

6-bromo-5-methoxy-2-methyl-2-vinylindolin-3-one (2o)

To a solution of 1-(2,4-dibromo-3-methoxyphenyl)-2-methylbut-3-en-1-one (0.1 g, 2.87 mmol) in DMSO, were added L-proline (6.62 mg, 0.57 mmol), $K_2CO_3$ (59.5.7 mg, 4.30 mmol), $CuSO_4 \cdot 5H_2O$ (14.35 mg, 0.57 mmol), sodium ascorbate (11.38 mg, 0.57 mmol), and $NaN_3$ (22.42 mg, 3.44 mmol). The mixture was stirred for 17 h at 70° C. (oil bath temperature). The reaction mixture was diluted with 30 mL of water and extracted with ethyl acetate (3×30 mL). Combined organic layer was dried ($Na_2SO_4$) and evaporated under reduced pressure. The crude was purified over silica gel (ethyl acetate and pet ether as eluent) to procure 2o (0.059 g, 2.09 mmol) in 72% yields.

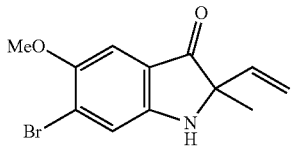

Yellow solid; 72% yield; $R_f=0.3$ (15% ethyl acetate/pet. ether); mp: 154-155° C.; IR ($CHCl_3$)v: 3284, 2923, 1740, 1671, 1577, 1478, 1275, 1154, 1040, 848, 718 cm$^{-1}$; $^1H$ NMR (500 MHz, $CDCl_3$): ☐ 1.44 (s, 3H), 3.84 (s, 3H), 4.43 (s, 1H), 5.15 (br d, J=10.4 Hz, 1H), 5.34 (br d, J=17.1 Hz, 1H), 5.85 (dd, J=10.4, 17.1 Hz, 1H), 7.05 (s, 1H), 7.20 (s, 1H); $^{13}C$ NMR (125 MHz, $CDCl_3$): ☐22.8 (q), 56.7 (q), 69.2 (s), 105.7 (d), 114.7 (t), 117.8 (d), 118.9 (s), 124.2 (s), 137.3 (d), 150.0 (s), 154.9 (s), 201.4 (s) ppm; HRMS (ESI+): calcd. for $C_{12}H_{12}BrNO_2H^+$ 282.0124, found 282.0129.

Advantages of the Invention

One-step synthesis of pseudo indoxyl derivatives;
Option to place a variety of substituents at all possible positions including the heterocyclic nitrogen;
Harsh reaction conditions avoided;
Reaction provides good yields of final product;
Compounds with fluorescing properties obtained.

We claim:

1. A one pot, one step process for preparation of compound of Formula 2,

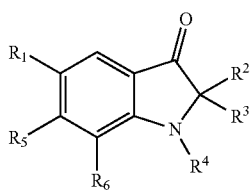

Formula 2 wherein, $R^1$, $R_5$ & $R_6$ represents independently H, —OMe, —N—OH, halo, alkyl(C1-C5) or NR(2) wherein R is selected from the group consisting of H, O, alkyl(C1-C5) and aryl;

$R_2$ represents independently alkyl (C1-C5), aryl, —CN, —$CO_2Et$, vinyl (CH=$CH_2$);

R3 represents independently alkyl(C1-C5), vinyl; or

R2 and R3 cyclize to form —CH2—$(CH_2)_n$—CH2— where n is 4,5,6;

R4 represents independently hydrogen, alkyl, —$(CH_2)_n$—Ar, —$(CH_2)_n$-CN, —$(CH_2)_n$—COOEt; —CH2=CH—CN;

n is 1, 2 and 3;

comprising the steps of:

i. mixing a compound of formula (1a)

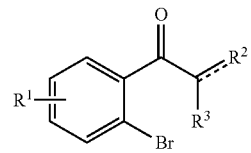

wherein $R^1$ represents independently H, —OMe, —N—OH, halo, alkyl(C1-C5) and NR(2) wherein R is selected from the group consisting of H, C, alkyl(C1-C5) and aryl;

$R_2$ represents independently alkyl (C1-C5), aryl, —CN, —$CO_2Et$, vinyl (CH=$CH_2$);

R3 represents independently alkyl(C1-C5), vinyl;

with sodium azide in the ratio ranging between 1.2 to 1.5 eq. in the presence of 15 to 25mol % copper catalyst, 15 to 25 mol % sodium ascorbate and 15 to 25 mol % L-proline, 1.5-2.0% of base and solvent followed by stirring to obtain compound of formula 2.

2. The process according to claim 1, wherein copper catalyst used is selected from the group consisting of $CuSO_4 \cdot 5H_2O$, CuI, $Cu_2O$ and $Cu(OAc)_2$.

3. The process according to claim 1, wherein copper catalyst used is $CuSO_4 \cdot 5H_2O$.

4. The process according to claim 1, wherein base used is selected from organic bases or from inorganic bases either alone or in combination thereof.

5. The process according to claim 1, wherein organic base is selected from the group consisting of pyridine, ethylamine, triethylamine ($Et_3N$), Triton B and TBAOH.

6. The process according to claim 1, wherein inorganic base is selected from the group consisting of alkali or alkaline earth metal hydroxides, carbonates or bicarbonates.

7. The process according to claim 1, wherein solvent used is selected from the group consisting of DMSO, DMF, acetone, ethyl acetate, THF polyethylene glycol either alone or in combination thereof.

8. The process according to claim 1, wherein the yield of compound of Formula 2 is in the range of 50 to 65%.

9. The process according to claim 1, wherein when R4 is alkyl said process is carried out in the presence of a compound of formula (3)

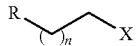

Formula 3 wherein X is a halide selected from Cl, Br, F or I,

R is alkyl and n=0,1 or 2 to obtain compound of formula 2.

10. The process according to claim 1, wherein the one pot $S_NAr$— Smalley cyclization of α, β-unsaturated ketones 1l-1n

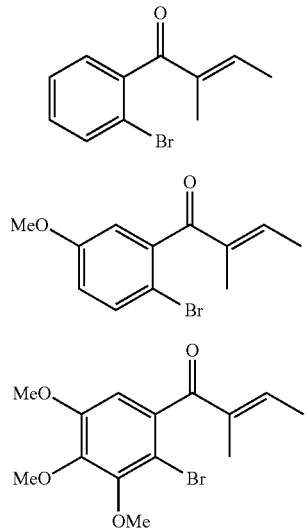

or β, γ-usaturated ketones 1o and 1p,

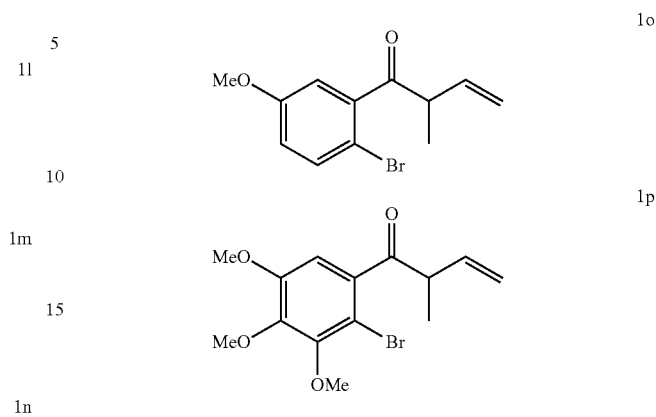

give exclusively 2-vinylindolin-3-one derivatives with >65% yield.

11. The process according to claim 1, wherein reaction between formula 1a and sodium azide is taking place for a period in the range of 15 to 17 hr at temperature in the range of 60-100° C. to obtain compound of formula 2.

* * * * *